(12) United States Patent
Yoshida

(10) Patent No.: US 6,393,092 B1
(45) Date of Patent: May 21, 2002

(54) X-RAY DETECTION DEVICE AND X-RAY CT APPARATUS

(75) Inventor: Minoru Yoshida, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 2 days.

(21) Appl. No.: 09/610,124

(22) Filed: Jul. 5, 2000

(30) Foreign Application Priority Data

Jul. 15, 1999 (JP) ........................................... 11-201725

(51) Int. Cl.[7] ................................................ G21K 1/12
(52) U.S. Cl. ................... 378/19; 378/98.8; 250/370.11; 250/370.09
(58) Field of Search ............ 378/18, 98.8; 250/370.09, 250/370.11; 257/431, 437, 443, 436

(56) References Cited

U.S. PATENT DOCUMENTS 4,819,074 A * 4/1989 Suzuki ......................... 358/209
5,636,299 A * 6/1997 Bueno et al. .................. 385/15

* cited by examiner

Primary Examiner—Robert H. Kim
Assistant Examiner—Jurie Yun
(74) Attorney, Agent, or Firm—Cooper & Dunham LLP

(57) ABSTRACT

In an X-ray detection device having an X-ray detection element array of photo diodes for multi channels arranged with a predetermined pitch on a substrate, a plurality of scintillators adhered onto respective photo diodes, and isolation walls disposed between neighboring scintillators for respective channels an isolation band for isolating the respective channels is provided between respective light receiving portions of the photo diode array for the multi channels, and the surface of the isolation band is covered by a material having light absorbing property, and the width of the region which is covered by the material having light absorbing property is equal to a region occupied by the width of the isolation wall provided between neighboring scintillators for the respective channels. Thereby, light leakage between the neighboring elements in a multi element X-ray detection device of scintillators and a silicon photo diode array is prevented to provide an X-ray detection device suitable for a multi slice type X-ray CT apparatus, in which the S/N ratio and spatial resolution of the device are enhanced by effectively guiding the light induced in the scintillators into the silicon photo diode array. An X-ray CT apparatus using such X-ray detection device can be provided.

14 Claims, 5 Drawing Sheets

X-RAY DETECTION DEVICE AND X-RAY CT APPARATUS

BACKGROUND

1. Field

The patent specification relates to an X-ray detection device which is used in an X-ray CT (computerized tomography) apparatus, and, in particular, relates to a multi element solid state X-ray detection device with a high spatial resolution and a high S/N ratio which is suitable for concurrently detecting X-ray transmission data of a plurality of slices of an object body being inspected

2. Related Art

Currently, the X-ray detection device used for an X-ray CT apparatus tends to be a solid state detection device using a scintillator that has improved X-ray detection accuracy in comparison with conventional X-ray detection using a xenon ionization detector, Such a solid state detection device comprises a multiplicity of channels of X-ray detection elements arranged in an arcuate shape around an X-ray source, each element being formed by a scintillator for converting incident X-ray into light and a light detection element such as a silicon photo diode which detects the light converted by the scintillator and outputs the same as an electrical signal.

In an X-ray CT apparatus, in order to improve throughput of the device, it is desired to shorten the time required to obtain CT images. The following two methods are generally enumerated;

(1) Shorten the time required for a rotation of a scanner.

(2) Increase the number of tomographic images taken for every rotation of a scanner.

With regard to (1) above, an improvement in rotating speed of the scanner can be achieved by reducing the weight of an X-ray tube serving as an X-ray generating device. On the other hand, the above (2) can be achieved by arranging a row of X-ray detection elements for an X-ray detection device conventionally arranged in one dimension in the channel direction in a plurality of rows, in that two rows or more than two rows are arranged along a slice direction (which is perpendicular to the channel direction).

Such an X-ray detection device is called a multi slice type X-ray detection device (the conventional X-ray detection device in which the X-ray detection elements are simply arranged in one dimension is generally called a single slice type X-ray detection device).

FIG. 8 shows a schematic diagram of an example of such a multi slice type X-ray detection device applied to a CT apparatus. In FIG. 8, a relationship between a multi slice type X-ray detection device 13, a body 11 to be inspected and an X-ray tube 10 is illustrated. The multi slice type X-ray detection device 13 has four rows of X-ray detection elements 12, from element row 1 to element row 4 arranged in slice direction, and can measure image data for a region covering four slices from slice 1 to slice 4 of the body 11 by concurrently receiving X-ray beams 14 irradiated from an X-ray tube 10. As a result, the utilization efficiency of the X-ray beams 14 from the X-ray tube 10 is improved four times in comparison with the conventional single slice type X-ray detection device. Further improvements in efficiency can be achieved as the number of X-ray detection element rows 12 increases.

With the background of conventional single slice type X-ray detection device, many of such multi slice type X-ray detection devices are constituted by simply arranging several single slice type X-ray detection device in the slice direction. However, in such a multi slice type X-ray detection device, the respective X-ray detection elements must match in performance. If they do not match sufficiently well, ring artifacts can appear in the reconstructed CT images and thereby deteriorate image quality.

Further, when the performance of X-ray detection elements varies in the slice direction, the measured data can differ depending on which X-ray detection element row in the slice direction obtained the measurements; therefore, it is possible, even when the measurements of image data are performed with regard to the same slice plane of the body 11, that the image quality of the CT images and medical information obtained from the CT images would vary. The obtained CT images should not differ because of differences in performance of X-ray detection elements used for the measurement, when image data are measured with regard to a same slice plane of a same body 11. For this reason, it is required that the X-ray detection elements are sufficiently matched in performance in bot the channel an the slice directions.

For the reasons explained above, it can be difficult to manufacture a multi slice type X-ray detection device that performs well.

Further, in order to match the performance characteristic values of the respective X-ray detection elements, it is important to reduce electrical cross talk as well as optical cross talk between respective neighboring elements in the detection device in addition to matching the performance characteristics of the scintillators and silicon photo diodes included in the respective elements.

FIG. 4 is a perspective view showing a basic structure of a conventional single slice type X-ray detection device.

In FIG. 4, numeral 1 is a scintillator which converts incident X-ray 5 into light, numeral 2a is an isolation wall between neighboring X-ray detection elements and numeral 3 is a silicon photo diode array which converts the light converted by the scintillators 1 into electrical signals. Each of the X-ray detection element is constituted by adhering a scintillator 1 on the upper surface of a respective photo receiving portion provided on the surface of the silicon photo diode array 3, and an X- ray detection element array is constituted by arranging the thus constituted X-ray detection elements in parallel with a predetermined pitch on a circuit substrate 6 while interleaving the isolation walls 2a therebetween. Further, numeral 7 is an upper face reflection plate which efficiently reflects light from the scintillators 1 and introduces the same toward the respective photo receiving portions on the silicon photo diode array 3.

In the above structured X-ray detection device, the incident X-ray on and into the detection device is converted by the scintillators 1 into visible light having a local intensity proportional to the local intensity of the incident X-ray 5. The converted light is transmitted through the scintillators 1 in part through reflection such as at the surface of the upper face reflection plate 7, the surfaces of the isolation walls 2a and boundaries and surfaces of the scintillators 1, and is introduced onto the photo receiving portions provided on the surface of the silicon photo diode array 3 in which a photo-electric conversion is performed and electrical signals (photo currents) having intensities proportional to the intensity of light, namely proportional to the intensity of X-ray is detected.

The performance of an X-ray detection device is evaluated primarily depending on S/N ratio and spatial resolution thereof. The S/N ratio is determined by the contribution rate of the incident X-ray 5 on the output signal, namely by the X-ray utilization efficiency and electrical signals (noise signals) induced in an electrical circuit system including the silicon photo diode array 3 when no X-ray is incident into the X-ray detection device. Then, the X-ray utilization efficiency is determined by a luminous efficiency (light conversion efficiency) of the scintillators 1, a light conversion efficiency of the silicon photo diode array 3, a spatial utilization efficiency which represents a spatial X-ray utilization efficiency by the X-ray detection device and a light transmission efficiency in the X-ray detection device.

Noise signals are primarily caused by shot noise and dark currents due to recombination currents in depletion layers in the silicon photo diode array 3 and noise currents in the electric current system such as a preamplifier. Among the causes which affect the above X-ray utilization efficiency, the luminous efficiency (light conversion efficiency) of the scintillators 1 and the light conversion efficiency of the silicon photo diode array 3 are determined in one to one relationship based on their physical properties. The spatial utilization efficiency can be improved by reducing the size of a region which does not contribute for the detection of the incident X-ray 5, such as spaces occupied by the solation walls 2a isolating between the respective X-ray detection elements, namely, the regions other than the scintillators 1. The light transmission efficiency can be improved by taking in more light into the light receiving portions, such as by reducing self absorption of light within the scintillators 1 and absorption of light at the surfaces of such as upper face reflection plate 7 and the isolation walls 2a as well as by reducing light reflection at the respective surfaces by providing an efficient optical coupling between the surfaces of scintillators 1 having a large refractive index and the surfaces of the light receiving portions of the silicon photo diode array 3.

The parameters which control the spatial resolution of the images to be reconstructed by making use of the X-ray data obtained with such X-ray detections devices are, from geometrical point of view, a distance between neighboring isolation walls 2a as shown in FIG. 4, defining an opening width of the respective X-ray detection elements, and, from electrical and optical points of view, are leakage of electrical signals between neighboring X-ray detection elements (hereinbelow called electrical cross talk) and leakage of X-ray or light therebetween (herein below called optical cross talk). Further, an image noise due to deterioration of S/N ratio can also be considered.

At first, with regard to the opening width of the respective X-ray detection elements representing the geometrical parameter, if the opening width is narrowed, the spatial resolution can be improved, In response to demands for higher spatial resolution, recent opening widths for the X-ray detection elements are below 1 mm. However, there is a limitation in that the amount of incident X-rays into the respective X-ray detection elements decreases when the opening is narrowed, thereby, the level of output signals from the respective X-ray detection elements reduces and the S/N ratio also decreases.

Further, when the opening width is narrowed, a ratio of the space occupied by the isolation walls 2a and the X-ray detection elements is reduced, thereby, the spatial utilization efficiency is also reduced, Still further, when the opening width is narrowed, the attenuation amount of the light generated from the scintillators 1 increases because of the self absorption thereof within the scintillators 1 and of a high repetition rate of light reflection at the surface of the upper face reflection plate 7 and at the surfaces of the isolation walls 2a, and the light transmission decreases. As a result, the level of the output signals of the X-ray detection device decreases and accordingly the S/N ratio also decreases.

When the electrical cross talk and the optical cross talk between the neighboring X-ray detection elements increase, the spatial resolution thereof decreases, and in order to reduce such cross talk the following measures have been taken conventionally. In order to reduce electrical cross talk in a multi elements silicon photo diode array, a measure as illustrated in FIG. 5 has been taken.

FIG. 5 shows a cross sectional structure of a common PIN type multi element silicon photo diode array. In FIG. 5, numeral 3a is an N+ layer of n type semiconductor, numeral 3b is an—layer of an intrinsic semiconductor which is formed by reducing the impurity density in a region spreading of a depletion layer and numeral 3c shows P+ layers of p type semiconductor serving as light receiving regions and being provided at a plurality of regions on the surface of the silicon photo diode array 3. Between the adjacent light receiving regions 3c I(N−) layer 3b' of dead zone is provided so as to electrically isolate the adjacent elements. Further, in order to ensure the electrical isolation by the I(N−) layer 3b' of dead zone, local n type semiconductor regions 3a' and a local p type semiconductor region 3c' are formed in the dead zone 3b' for an isolation. Further, in FIG. 5 numeral 3d is an anode electrode for an individual photo diode element in that a silicon photo diode, numeral 3e is a reflection preventing film for the respective silicon photo diodes and numeral 3f is a protective oxide film.

Further, as measures for preventing optical cross talk between neighboring elements, a measure as illustrated in FIG. 6 has been proposed, where a light reflecting member 2b of white color pigment serving as an isolation wall is filled in a narrow gap between the neighboring scintillators 1 as disclosed in JP-A-58-219471(1983), and another measure as illustrated in FIG. 7 has been proposed, where a metal isolation wall 2b' is inserted between the neighboring scintillators 1 as disclosed in JP-B-2720159(1997), and JP-B-2720162(1997).

The above referred to conventional measures for reducing the optical cross talk present the following problems.

In the structure as shown in FIG. 6 and as disclosed in JP-A-58-219471(1983), optical cross talks between scintillators 1 is reduced by means of reflecting members 2b between the scintillators 1. It is technically difficult to uniformly fill the light reflecting member 2b serving as an isolation wall in the narrow gaps between the scintillators 1 and when bubbles are mixed therein, which causes variation in sensitivity, nonuniform sensitivity distribution and optical leakage can occur. Further, since there is no optical isolation at an adhesion layer 4 adhering the scintillators 1 and the silicon photo diode array 3, a problem arises that an optical leakage is caused through the adhesive layer 4.

Further, in the structure as illustrated in FIG. 7 and as disclosed in JP-B-2720159(1997), after adhering the scintillators 1 onto the silicon photo diode array 3 via the adhesive layer 4, gaps for isolating the respective X-ray detection elements are formed up to the inside of the silicon photo diode array 3 so as to insert metallic isolation walls 2b', therefore, a possible positional deviation between the respective scintillators 1 and the respective silicon photo diodes in the silicon photo diode array 3 is prevented, and in addition since the metallic isolation walls 2b' are inserted inside the silicon photo diode array 3, an advantage of preventing optical leakage between neighboring X-ray detection elements is achieved. On the other hand, because of microcracks caused when the surface of the silicon photo diode array 3 is cut, leakage currents and dark currents in the silicon photo diodes increase which causes problems such as reducing S/N ratio and characteristic deviation of the respective X-ray detection elements. When applying the conventional measures for reducing electrical and optical cross talks having the above explained problems to a multi slice type X-ray detection device, the following problems will be further caused.

Namely, for constructing a multi slice type X-ray CT apparatus, it is necessary to form a two dimensional multi elements X-ray detection device in which X-ray detection elements are arranged in a plurality of rows in channel and slice directions as illustrated in FIG. 8. When realizing such two dimensional multi elements X-ray detection device, it is necessary to constitute the silicon photo diode array serving as a photo-electric conversion element in a two dimensional multi elements structure, and when it is required to improve the spatial resolution with such two dimensional multi elements structure, it is necessary to increase packing density of the silicon photo diode array.

Accordingly, in the multi slice type X-ray detection device, it is necessary to provide measures for increasing the packing density thereof such as decreasing an area occupied by the silicon photo diode array as well as using a part of the array as a region for wirings. However, If the conventional measures as disclosed such as in JP-A-58-219471(1983) and JP-B-2720159(1997) are used for the multi slice type X-ray detection device including above explained packing requirements, an improvement in packing density while ensuring a predetermined spatial resolution and S/N ratio will be limited.

SUMMARY OF THE INVENTION

An object of the present invention is to provide an X-ray detection device, in particular a multi element solid state X-ray detection device which is suitable for a multi slice type X-ray CT apparatus which reduces electrical and optical cross talk between respective neighboring X-ray detection elements, increases a packing density, equalizes the characteristics of the respective X-ray detection elements, and to provide an X-ray CT apparatus using such X-ray detection device.

The above object is achieved by one of or a combination of the following measures.

(1) In a multi element solid state detection device which is provided with an X-ray detection element array constituted by an array of photo diodes for multi channels arranged with a predetermined pitch on a substrate, a plurality of scintillators each being adhered onto the respective photo diodes for every channel and isolation walls disposed between the neighboring scintillators for respective channels, an isolation wall or band for isolating the respective channels is provided between respective light receiving portions of the photo diode array for the multi channels, and the surface of the isolation wall or band is covered by a material having light absorbing property.

(2) The width of region which is covered by the material having light absorbing property is equal to a region occupied by the width of the isolation wall provided between neighboring scintillators for the respective channels, smaller than a width region of respective scintillators including the corresponding isolation walls not contributing to X-ray detection, or larger than the thickness of the adhesive layer adhering the photo diode array and the scintillators for every channel.

(3) A reflection preventing film is provided on the surface of the respective light receiving portions of the photo diode array, and the refractive index of the adhesive layer adhering the photo diode array and the scintillators is smaller than the refractive index of the scintillators and the refractive index of the reflection preventing film.

(4) The isolation wall or band includes on the surface thereof a region covered by the material having light absorbing property and another region covered by a tight reflecting film.

(5) The width of the region on the surface of the isolation wall or band including the region covered by the material having light absorbing property and the region covered by the light reflecting film is larger than the width of the isolation wall.

(6) The material having light absorbing property provided on the surface of the isolation wall or band is carbon or carbon compound.

(7) The material having light absorbing property provided on the surface of the isolation wall or band is one selected from the group of sulfides such as $Ag_2S$, FeS, NiS and $Mo_2S_3$ or any combinations thereof.

(8) The material having light absorbing property provided on the surface of the isolation wall or band is one selected from the group of oxides such as $O_sO$, CrO, SnO, Teo, $Pb_2O$, NbO, BiO, MoO and RuO or any combinations thereof.

(9) An X-ray CT apparatus which uses the X-ray detection device as referred to (1)~(8) above.

With the thus structured X-ray detection device according to the present invention, light generated in the respective isolated scintillators that would leak through the adhesive layer to the respective neighboring scintillators or the respective neighboring light receiving portions on the photo diode array, is absorbed by the material having light absorbing property provided on the surface of the isolation wall or band. Accordingly, the light which reaches the isolation wall or bands is substantially absorbed by the light absorbing material, and light leakage between the neighboring X-ray detection elements is eliminated, thereby, the spatial resolution of the device is enhanced. Further, it is unnecessary to cut and separate the respective X-ray detection elements down to the inside of the silicon photo diode array as has been explained in connection with JP-B-2720159(1997), and so deterioration in S/N ratio and deviation of characteristics of the respective X-ray detection elements induced by increased leakage currents and dark currents in the respective silicon photo diodes due to causes such as microcracks caused during the processing thereof are also eliminated. Accordingly, an X-ray detection device which permits an efficient conversion of X-ray energy into electrical signals can be realized, thereby, when such an X-ray detection device is applied to an X-ray CT apparatus, in particular to a multi slice type X-ray CT apparatus which necessitates great many number of X-ray detection elements, tomographic images of high quality for a plurality of slices can be obtained concurrently.

DETAILED DESCRIPTION OF THE PREFERRED EMBODIMENTS

Figure 1:
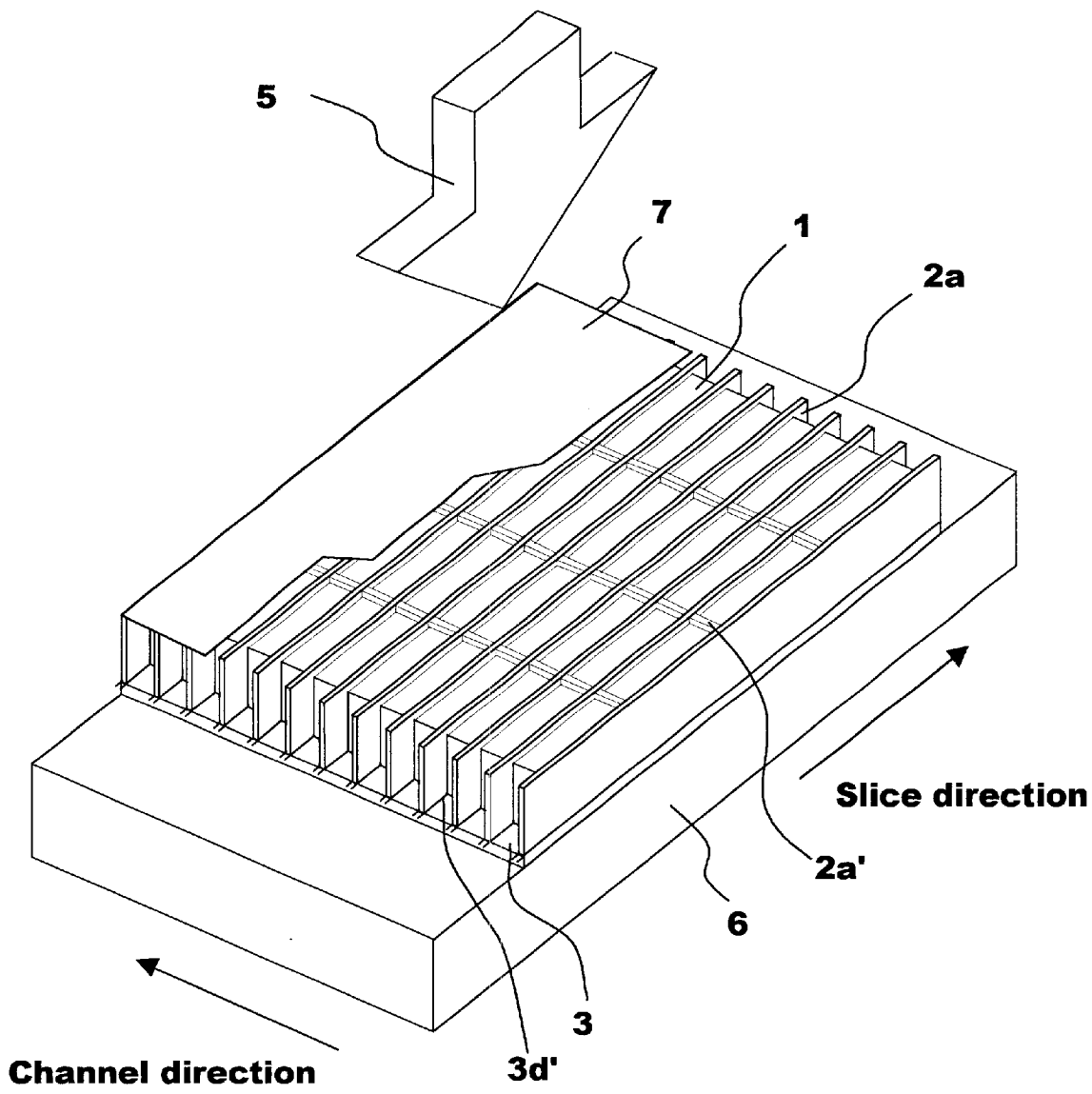
FIG. 1 is a perspective view showing structure of a two dimensionally arranged multi element X-ray detection device used as an X-ray detection device in a multi slice CT apparatus according to the present invention.

Hereinbelow, embodiments according to the present invention will be explained in detail with reference to FIGS. 1 through 3, in which the same or equivalent elements are designated by the same reference numerals.

In FIG. 1, numeral 5 shows an incident X-ray beam, and numeral 7 shows an upper face reflection plate which is provided for shielding external light incident to the X-ray detection device and for efficiently reflecting light generated in the scintillators 1 so as to guide the same to the silicon photo diode array 3. Within the X-ray detection device, a two dimensionality arranged X-ray detection element array is constituted by arranging on a circuit substrate 6 a great many X-ray detection elements which are formed by adhering a corresponding number of scintillators 1 on respective light receiving portions provided on the surface of a two dimensional silicon photo diode array 3 in a two dimensional manner, in parallel and at a predetermined pitch, together with isolation walls 2a in a channel direction and with isolation walls or bands 2a' in a slice direction, both of which are made of a material as a metal or an organic material having a high refractive Index. The two dimensionally arranged X-ray detection element array according to the present embodiment is illustrated as including 12 channels and 4 slices. However, an actual multi slice type X-ray detection device includes 40 blocks of two dimensionally arranged X-ray detection element arrays and each array includes X-ray detection elements for covering 24 channels. Accordingly, with an X-ray CT apparatus mounting an X-ray detection device incorporating the two dimensionally arranged X-ray detection element array, a multi slice type X-ray CT apparatus which produces through one scanning at once tomographic images for 4 slices (4 cross sections) can be constituted. Possible electrical and optical cross talk in the thus constituted two dimensionally arranged solid state X-ray detection device is reduced by the means shown in FIGS. 2 and 3 which will be explained herein below.

Figure 2:
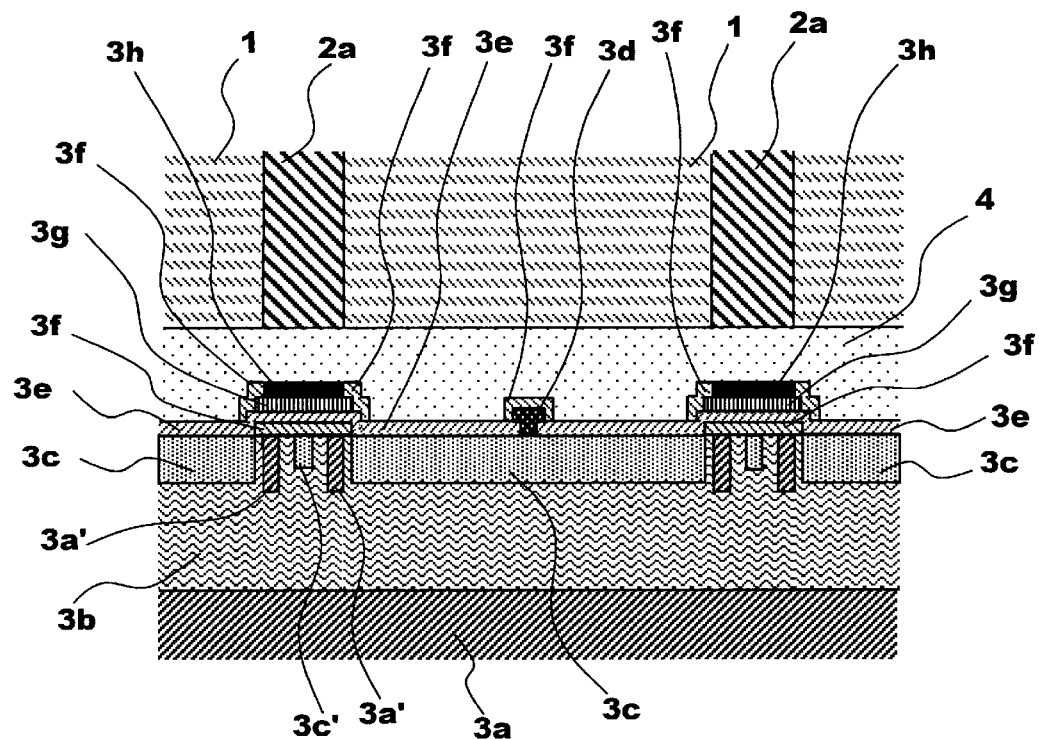
FIG. 2 is a cross sectional view taken along a channel direction of a first embodiment according to the present invention of the two dimensionally arranged multi element X-ray detection device as schematically illustrated in FIG. 1.

In FIG. 2, numeral 1 is a scintillator which converts incident X-ray into light, numeral 2a is an isolation wall which optically separates and isolates between the neighboring scintillators 1, numeral 3 including 3a~3g is a two dimensionally arranged silicon photo diode array which converts the light converted by the scintillators 1 into electrical signals, numeral 4 is an adhesive layer which couples optically and mechanically the scintillators 1 and the isolation walls 2a with the two dimensionally arranged silicon photo diode array 3.

In order to realize a high quantum efficiency and a high speed response, it is preferable for the two dimensionally arranged silicon photo diode array 3 to use a PIN type silicon photo diodes each of which includes an intrinsic semiconductor layer 3b having a reduced impurity density in an intermediate depletion layer expanding region between a p type semiconductor layer 3c and an n type semiconductor layer 3a. Further, in order to improve S/N ratio of the X-ray detection device by reducing capacitances and dark currents of the silicon photo diodes, it is preferable to use an epitaxial substrate for the substrate of the PIN type silicon photo diodes.

The refractive index of the p type semiconductor layer 3c serving as the light receiving region is large, such as n≈3.5, and the refractive index of the adhesive layer 4 which is the medium contacting to the surface of the p type semiconductor layer 3c is small, such as n≈1.5, therefore, the difference therebetween becomes large, for this reason, the critical angle with respect to incident light decreases and light reflection at the surface of the p type semiconductor layer 3c increases.

Therefore, in order to cause efficient light incident a reflection preventing film 3e such as SiN and SiO$_2$ film having a refractive index n of about 2.1~2.7 is provided on the surface at the light incident side of the p type semiconductor layer 3c. Further, on a part of the surface of the p type semiconductor layer 3c serving as the light receiving region an anode electrode 3d of a material such as Al thin film for taking out signal currents (photo currents) is provided, and the surface thereof is covered by a protective film 3f such as SiO$_2$ for the purpose of corrosion prevention.

Now, the present embodiment will be explained more specifically by indicating actual sizes of the respective portions. When assuming an arrangement pitch of the respective X-ray detection elements in the channel direction as 1 mm, it is preferable to provide an opening width of the X-ray detection element, in which the width of the scintillator 1 is 0.9 mm, and the width of the isolation wall 2a is 0.1 mm. On the other hand, with regard to the dimension of the silicon photo diode array to be combined with the scintillators 1 together with the isolation walls 2a, when assuming that the pitch between the neighboring light receiving portions in the form of p type semiconductor layer 3c is 1 mm, it is preferable to set the width of the light receiving porion in the form of p type semiconductor layer 3c in a range of 0.7 mm~0.8 mm which is narrower than the opening width of 0.9 mm of the X-ray detection element. Further, all of the surface of the light receiving portions in the form of p type semiconductor layer 3c are covered, for the purpose of efficient light incidence, by the reflection preventing film of transparent optical thin film 3e having refractive index n of about 2.1~2.7 such as SiN film and SiO$_2$ film.

The width of a dead zone 3b', where no p type semiconductor layer is formed and an i type semiconductor region remains which is provided between the neighboring light receiving portions in the form of p type semiconductor layer 3c for separating the neighboring X-ray detection elements, is made as 0.3 mm, alternatively, when the width of the light receiving portion is 0.8 mm, the width of the dead zone is made as 0.2 mm, which width is usually larger than the width of the above isolation wall 2a. Further, in order to prevent electrical cross talk and to ensure electrical separation between the neighboring silicon photo diodes an n type semiconductor region $3a'$, a p type semiconductor region $3c'$ and another n type semiconductor region $3a'$ having a width of 0.03 mm~0.05 mm are locally formed in the dead zone $3b'$ with a predetermined distance, alternatively, when the width of the light receiving portion is 0.8 mm, the width of the locally formed n and p type regions is 0.02 mm~0.03 mm, further, over the dead zone $3b'$ on the substrate a first insulating protection film $3e$ such as SiN film, a second insulative protection film $3f$ such as $SiO_2$ film and a third light shielding and reflecting film $3g$ such as Al and Ag film for shielding light incident to the dead zone are provided, with respective width substantially the same as of the dead zone $3b'$, i.e., 0.3 mm, as an alternative, when the width of the light receiving portion is 0.8 mm, the width of the first through third films is 0.2 mm. Further, over the third film $3g$ and at the center portion in the width direction as a fourth layer a light absorbing film $3h$ such as carbon film having the same or slightly narrower width than that of the isolation wall $2a$, i.e., 0.1 mm or slightly less than 0.1 mm, is provided. It is preferable that the width of the light absorbing film $3h$ never exceeds the width of the isolation wall $2a$. Further, at both side portions in the width direction of the light absorbing film of a material such as carbon film, protective films $3f$ of transparent optical thin film such as $SiO_2$ film are provided in such a manner as to sandwich the light absorbing film $3h$ in the width direction. When the width of the dead zone $3b'$ is 0.3 mm, the width of the protective film $3f$ of a material such as $SiO_2$ film is equal to 0.1 mm or more, alternatively, when the width of the dead zone $3b'$ is 0.2 mm, the width of the protective film $3f$ is 0.05 mm or more. Since a light reflection rate of the surface of these protective films $3f$ is high, i.e., more than 80%, even if the width of the dead zone $3b'$ is larger than the width of the isolation wall $2a$ and extends into the region of the scintillator 1, a possible loss of light due to absorption by the surface of the protective films $3f$ can be reduced.

Although it is ideal to use for the light absorbing film $3h$, a material that fully absorbs the light coming from the scintillators 1, materials that are black, charcoal gray and dark brown, such as carbon (C) and carbon compounds, are usually used. As film forming methods for the light absorbing film $3h$, the following methods can be used; a method of forming a carbon (C) film through PVD or a spattering, a method of forming a silicon carbide (SiC) film through CVD, and a method of forming a silver sulfide ($Ag_2S$) film by reacting with sulfur or a method of forming a silver sulfide ($Ag_2S$) film by acting hydrogen sulfide ($H_2S$) onto a silver (Ag) film, when silver (Ag) is used as an under layer light reflecting film. Other than the above light absorbing materials giving black color, charcoal gray or dark brown, sulfides such as FeS, NiS and $Mo_2S_3$ and oxides such as OsO, CrO, SnO, TeO, $Pb_2O$, NbO, BiO, MoO and RuO can be used.

Further, as the material for the adhesive layer 4 which couples optically and mechanically the scintillators 1 and the isolation walls $2a$ with the two dimensionally arranged silicon photo diode array 3, an epoxy resin which shows a high transparency, a stability with regard to X-ray and a refractive index of $n \geq 1.5$, can be used, for example. Such a composition preferably includes a bisphenol A epoxy resin as a main component, a polyamide curing agent of 3, 9-bis (3-aminopropyl) - 2, 4, 8, 10-tetrapyro [5.6] undecane (ATU), a reactive diluent for adjusting viscosity and a silan coupling agent as a resin modifier. The thickness of the adhesive layer 4 affects the degree of optical cross talk, in that if the thickness is too great, cross talk increases, and if the thickness is too little, bubbles tend to be mixed therein and the mechanical strength of the layer decreases. For this reason, thickness selection of the adhesive layer 4 is important, therefore, it is preferable to make the thickness of the adhesive layer 4 less than ½ of the width of the isolation wall $2a$, so that when the width of the isolation wall $2a$ is 0.1 mm, it is preferable to make the thickness of the adhesive layer less than 0.05 mm and more practically in a range of 0.01 mm~0.02 mm.

Figure 3:
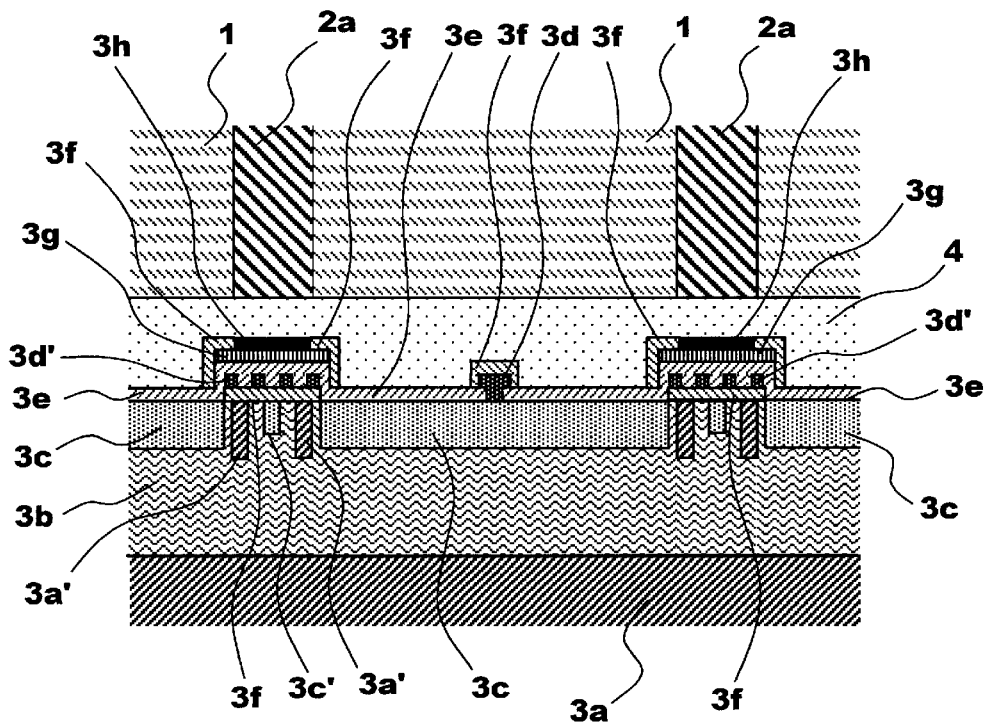
FIG. 3 is a cross sectional view taken along a channel direction of a second embodiment according to the present invention of the two dimensionally arranged multi element X-ray detection device as schematically illustrated in FIG. 1.
Figure 4:
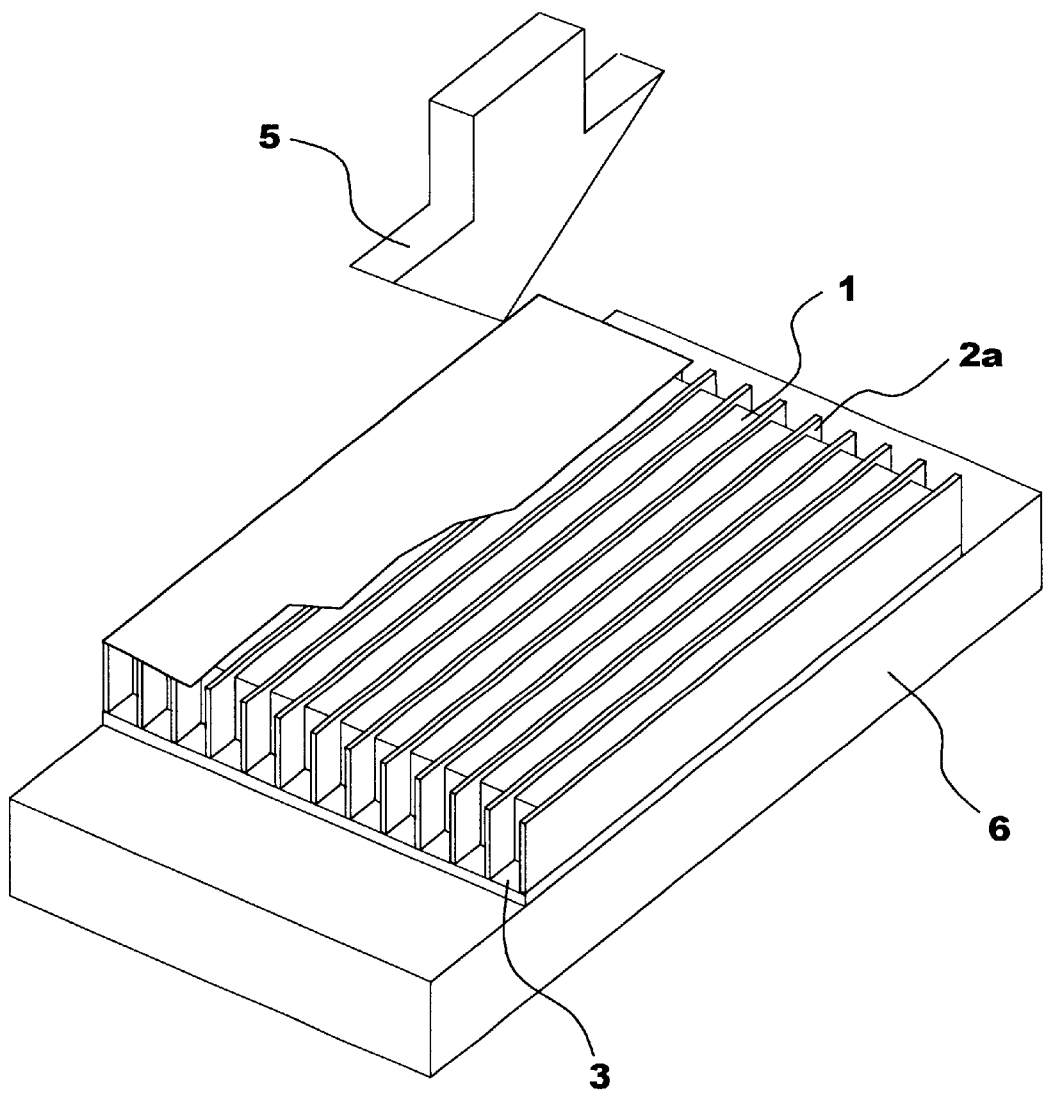
FIG. 4 is a perspective view showing a basic structure of a conventional multi element solid state X-ray detection device.
Figure 5:
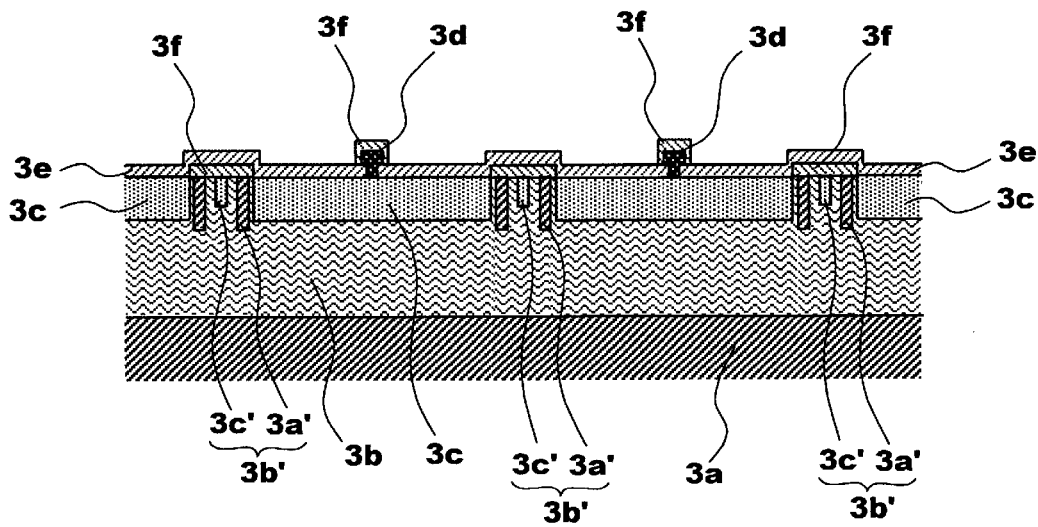
FIG. 5 is a cross sectioned structural diagram of a common PIN type multi element silicon photo diode array used for a conventional multi element solid state X-ray detection device.
Figure 6:
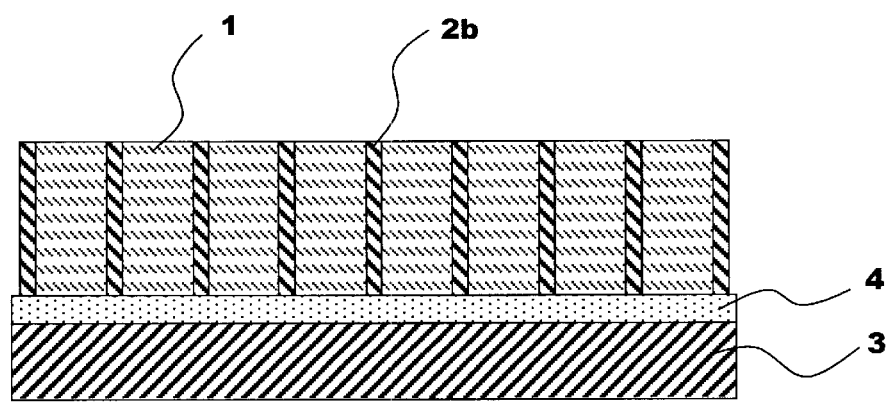
FIG. 6 is a cross sectioned structural diagram of a multi element solid state X-ray detection device as disclosed in a first prior art.
Figure 7:
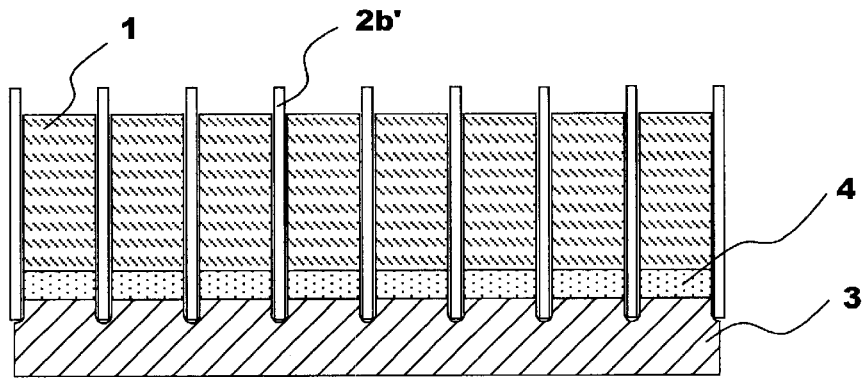
FIG. 7 is a cross sectioned structural diagram of a multi element solid state X-ray detection device as disclosed in a second prior art.
Figure 8:
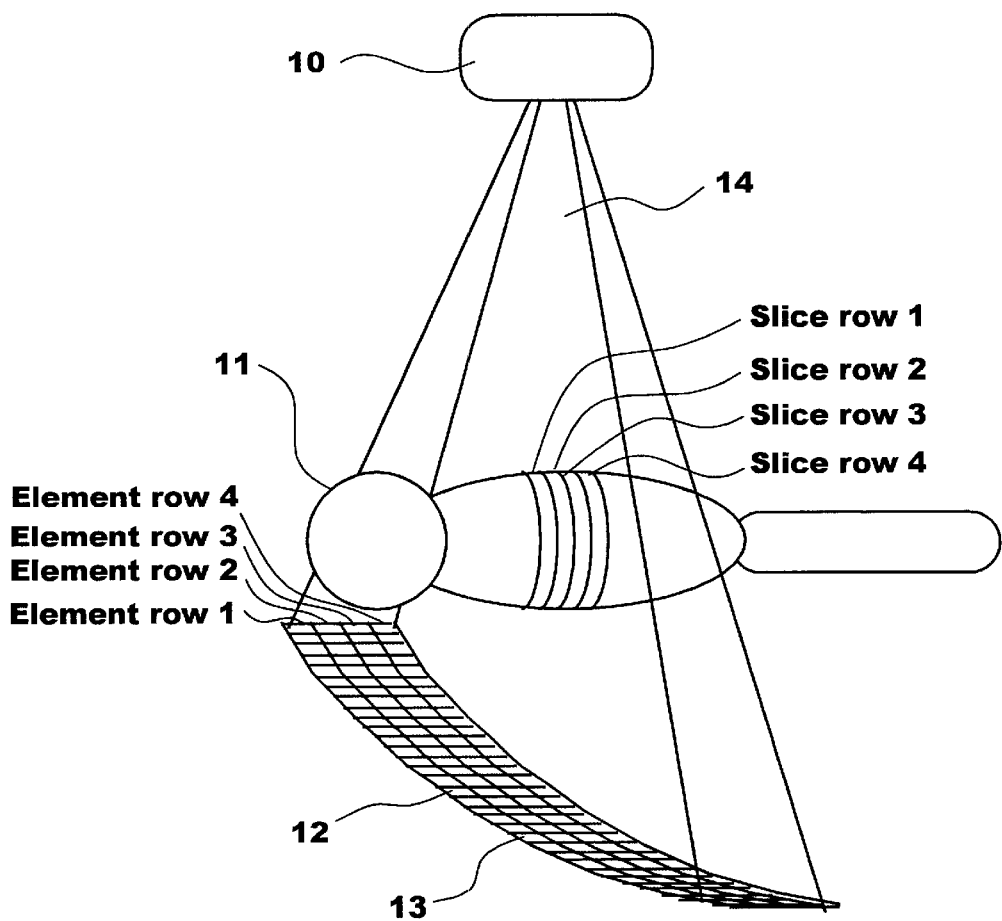
FIG. 8 is a schematic diagram illustrating a manner of application of a multi slice type X-ray detection device according to the present invention to an X-ray CT apparatus.

FIG. 3 is a cross sectional view taken along a channel direction of a second embodiment according to the present invention of the two dimensionally arranged multi element X-ray detection device as schematically illustrated in FIG. 1. In FIG. 3, other than the structure of the dead zone for separating photo diode elements located between neighboring light receiving portions in the form of p type semiconductor layer $3c$ in the two dimensionally arranged silicon photo diode array which is formed by integrating in a matrix shape the light receiving portions in the form of p type semiconductor layer on a common silicon substrate, the structure of the X-ray detection element array is substantially the same as that of the first embodiment as shown in FIG. 2, and the same reference numerals in FIG. 3 as in FIG. 2 designate the same or equivalent portions as in FIG. 2. At the portion of the dead zone $3b'$ a plurality of signal leading out wires $3d'$, such as Al thin film interconnects, which are to be connected to the anode electrode $3d$ as Al thin film for taking out the signal currents (photo currents) of the respective light receiving portions in the form of p type semiconductor layer and are also illustrated in FIG. 1, are formed on the substrate surface of the dead zone $3b'$ via an insulative oxide film $3e$.

The surfaces of the signal leading out wires $3d'$ are covered by the insulative film $3f$, and the surface of the insulative film $3f$ is covered by the shielding and light reflecting film $3g$ of a material such as Al and Ag for shielding the light incident into the dead zone $3b$, as in the first embodiment. Further, on the surface of the shielding and light reflecting film $3g$ the regions covered by the protective film $3f$ such as $SiO_2$ film and the region covered by the light absorbing material, a light absorbing film $3h$ such as carbon film can be provided.

According to the embodiments as shown in FIGS. 2 and 3, the light generated by the scintillators 1 in the X-ray detection element array passes through the scintillators 1 after repeated reflections at the surfaces of the isolation walls $2a$ and the upper face reflection plate 7 and at the boundaries and the surfaces of the scintillators 1, and is emitted into the adhesive layer 4, further the emitted light passes through the adhesive layer 4 and is introduced into the respective light receiving portions in the form of p type semiconductor layer $3c$, in the silicon photo diode array where the received light is photo-electrically converted and is detected as electrical signals (photo currents). Now, all of the light emitted into the adhesive layer is not necessarily directed toward the respective light receiving portions in the form of p type semiconductor layer $3c$, some of the light advances in the adhesive layer 4 in the lateral direction, and is directed toward the neighboring elements. The difference in refractive index between the adhesive layer 4 ($n \approx 1.5$) and the reflection preventing film $3e$ ($n \approx 2.1$~2.1) provided on the light incidence surface of the respective light receiving portions is large, thus, the critical angle with respect to incident light onto the respective light receiving portions assumes a small angle below 40°, therefore, incident light from lateral direction with a large incident angle will mostly be reflected at the surface of the reflection preventing film $3e$ to prevent incidence into the neighboring light receiving regions, however, light with a small incident angle falling within the critical angle may reach the neighboring light receiving regions to cause optical cross talk.

However, according to the embodiments of the present invention, on the surface of the dead zone for separating photo diode elements located between neighboring light receiving portions in the form of p type semiconductor layer 3c in the two dimensionally arranged silicon photo diode array a region covered by the light absorbing material, the light absorbing film 3h is provided. Accordingly, when light generated in the respective isolated scintillators would otherwise leak through the adhesive layer to the respective neighboring scintillators or the respective neighboring light receiving portions on the photo diode array, such light is absorbed by the material having light absorbing property provided on the surface of the isolation wall or band, when the light passes through the respective isolation bands provided between the respective neighboring light receiving portions on the photo diode array. Accordingly, the light which reaches the isolation bands is substantially absorbed by the light absorbing material, and light leakage between the neighboring X-ray detection elements is eliminated, thereby, a possible deterioration of the spatial resolution due to optical cross talks of the device is prevented. Further, at both side portions in the width direction of the light absorbing film 3h, since the protective films 3f of transparent optical thin film having a light reflection rate of more than 80% are provided in such a manner as to sandwich the light absorbing film 3h in the width direction, and because a film of a material such as Al and Ag having a high reflection rate is provided as an under layer for the optical thin film, the reflection rate of the protective film 3f is enhanced, even if the width of the dead zone 3b' is set larger than the width of the isolation wall 2a and extends into the region of the scintillator 1, a possible loss of light due to absorption by the surface of the protective films 3f can be reduced.

Further, with the structure according to the present embodiments, since the necessity of cutting up to the inside of the silicon photo diode array 3 so as to separate the respective X-ray detection elements as has been explained in connection with JP-B-2720159 (1997) is avoided, problems such as of decreasing S/N ratio and characteristic deviation of the respective X-ray detection elements caused by such as increased leakage currents and dark currents in the silicon photo diodes due to microcracks caused when performing the cutting processing, are eliminated.

In the above explanation of FIGS. 2 and 3 embodiments, in order to avoid duplicate explanation, only the provision of the dead zones with the light absorbing film 3h between the X-ray detection elements arranged in the channel direction has been explained, however, the same is true with regard to X-ray detection elements arranged in the slice direction, and through the combination of both, a multi slice type X-ray detection device is constituted.

As has been explained hitherto, in the multi element solid state X-ray detection device according to the present invention, on the surfaces of the isolation bands for separating photo diode elements located between neighboring light receiving portions in the form of p type semiconductor layer 3c in the silicon photo diode array for multi channels a region covered by the light absorbing material is provided. Accordingly, when light generated in the respective isolated scintillators separated by the respective isolation walls would otherwise leak through the adhesive layer to the respective neighboring scintillators or the respective neighboring light receiving portions on the photo diode array, such light is absorbed by the material having light absorbing property provided on the surface of the isolation wall or bands, when the light passes through the respective isolation wall or bands provided between the respective neighboring light receiving portions on the photo diode array. Accordingly, light which reaches the isolation bands is substantially absorbed by the light absorbing material, and light leakage between the neighboring X-ray detection elements is eliminated, thereby, a possible deterioration of the spatial resolution due to optical cross talks of the device is prevented.

Still further, as has been explained in connection with the FIG. 3 embodiment, since the isolation wall or bands are also utilized as the wiring regions, a packing density of the X-ray detection element array is enhanced.

Further, according to the present invention, the necessity of cutting up to the inside of the silicon photo diode array 3 so as to separate the respective X-ray detection elements as has been explained in connection with JP-B-2720159 (1997) is avoided, thereby, the problems such as of decreasing S/N ratio and characteristic deviation of the respective X-ray detection elements caused by such as increased leakage currents and dark currents in the silicon photo diodes due to such as microcracks caused when performing the cutting processing, are eliminated.

Still further, according to the present invention, when using the multi element solid state X-ray detection device provided with the electrical and optical cross talk reducing means and the packing density enhancing means as has been explained hitherto in an X-ray CT apparatus, in particular, in a multi slice type X-ray CT apparatus which requires great many number of X-ray detection elements, tomographic images with a high quality for a plurality of slices can be obtained concurrently.

What is claimed is:

1. A multi element solid state X-ray detection device comprising: an X-ray detection element array which includes an array of photo diodes for multi channels arranged with a predetermined pitch on a substrate, a plurality of scintillators each being adhered onto the respective photo diodes for every channel and isolation walls disposed between the neighboring scintillators for respective channels, wherein an isolation band for isolating the respective channels is provided between respective light receiving portions of the photo diode array for the multi channels, and the surface of the isolation band is covered by a material having light absorbing property.

2. A multi element solid state X-ray detection device according to claim 1, wherein the width of the region which is covered by the material having light absorbing property is equal to a region occupied by the width of the isolation wall provided between the neighboring scintillators for the respective channels, smaller than a width region of respective scintillators including the corresponding isolation walls not contributing to X-ray detection, or larger than the thickness of the adhesive layer adhering the photo diode array and the scintillators for every channel.

3. A multi element solid state X-ray detection device according to claim 2, further comprises a reflection preventing film formed on the surface of the respective light receiving portions of the photo diode array, and wherein the refractive index of the adhesive layer adhering the photo diode array and the scintillators is determined smaller than the refractive index of the scintillators and the refractive index of the reflection preventing film.

4. An X-ray CT apparatus which uses the multi element solid state X-ray detection device according to claim 1.

5. An X-ray CT apparatus which uses the multi element solid state X-ray detection device according to claim 2.

6. An X-ray CT apparatus which uses the multi element solid state X-ray detection device according to claim 3.

7. An X-ray detection device comprising:
   a silicon photo diode array which includes a plurality of light receiving portions arranged on a substrate along both channel direction and slice direction perpendicular to the channel direction with a predetermined pitch and an isolation band with a predetermined width which separates respective neighboring light receiving portions;
   a scintillator which is optically coupled with each of the respective light receiving portions via a adhesive layer;
   an isolation wall which is disposed between respective neighboring scintillators so as to oppose to the corresponding isolation band on the silicon photo diode array; and
   a light absorbing film which covers a portion on the isolation band on the silicon photo diode array opposing to the isolation wall with a width not more than the width of the isolation wall.

8. An X-ray detection device according to claim 7, wherein the predetermined width of the isolation band is determined larger than the width of the isolation wall.

9. An X-ray detection device according to claim 8, wherein both end portions on the isolation band not covered by the light absorbing film are respectively covered by a light reflecting film.

10. An X-ray detection device according to claim 7, further comprises a reflection preventing film formed on the surface of the respective light receiving portions of the silicon photo diode array, and wherein the refractive index of the adhesive layer adhering the silicon photo diode array and the scintillators is determined smaller than the refractive index of the scintillators and the refractive index of the reflection preventing film.

11. An X-ray detection device according to claim 7, further comprises a plurality of signal taking out leads for respective silicon photo diodes in the silicon photo diode array are wired in the isolation band.

12. An X-ray detection device according to claim 7, further comprises a light shielding and reflecting film is disposed beneath the light absorbing film on the isolation band.

13. An X-ray detection device according to claim 7, wherein the thickness of the adhesive layer is determined less than ½ of the width of the isolation wall.

14. An X-ray detection device comprising, an X-ray detection element array including a plurality of X-ray detection elements which are arranged on a substrate along both channel direction and slice direction perpendicular to the channel direction with a predetermined pitch; and a reflection plate which is disposed over an upper face of the X-ray detection element array at an X-ray incident side,
   wherein the X-ray detection element array is constituted by:
   a silicon photo diode array which includes a plurality of silicon photo diode elements having light receiving portion arranged on the substrate along both channel direction and slice direction perpendicular to the channel direction with a predetermined pitch and an isolation band with a predetermined width which electrically separate respective neighboring silicon photo diode elements;
   a scintillator which is optically coupled with each light receiving portion of the respective silicon photo diode elements;
   an isolation wall for optically separating the neighboring scintillators which is disposed between respective neighboring scintillators so as to oppose to the corresponding isolation band on the silicon photo diode array;
   an adhesive layer which adheres the respective scintillators and isolation walls at predetermined positions on the silicon photo diode array; and
   a light absorbing film which covers a portion on the isolation band on the silicon photo diode array opposing to the isolation wall with a width not more than the width of the isolation wall.

* * * * *